United States Patent [19]

Nomura et al.

[11] Patent Number: 5,349,115
[45] Date of Patent: Sep. 20, 1994

[54] DIMERIZATION OF LOW α-OLEFINS

[75] Inventors: Kotohiro Nomura, Osaka; Masaru Ishino, Chiba; Michio Yamamoto, Shiga; Gohfu Suzukamo; Makoto Itagaki, both of Osaka, all of Japan

[73] Assignee: Sumitomo Chemical Co., Ltd., Osaka, Japan

[21] Appl. No.: 57,843

[22] Filed: May 7, 1993

[30] Foreign Application Priority Data

May 8, 1992 [JP] Japan ................. 4-116044
May 8, 1992 [JP] Japan ................. 4-136730
Jun. 8, 1992 [JP] Japan ................. 4-147202
Oct. 8, 1992 [JP] Japan ................. 4-270087
Dec. 25, 1992 [JP] Japan ................. 4-346027

[51] Int. Cl.$^5$ ............................................ C07C 2/24
[52] U.S. Cl. ............................ 585/513; 585/520; 585/526; 585/527
[58] Field of Search ...................... 585/510–515, 585/520, 522, 526, 531, 527

[56] References Cited

U.S. PATENT DOCUMENTS 4,487,847 12/1984 Knudsen ..................... 502/155
4,709,112 11/1987 Sato et al. ................... 585/513
4,992,610 2/1991 Sato et al. ................... 585/511

FOREIGN PATENT DOCUMENTS 54-39004 3/1979 Japan .
57-167932 10/1982 Japan .
57-169433 10/1982 Japan .

OTHER PUBLICATIONS

Chemical Abstract, 98: 88802v, 1983.
Chemical Abstract, 98: 106775v, 1983.

Primary Examiner—Asok Pal
Assistant Examiner—P. Achutamurthy
Attorney, Agent, or Firm—Birch, Stewart, Kolasch & Birch

[57] ABSTRACT

A process for preparing a dimer of a lower α-olefin in the presence of Catalyst (A) containing a nickel compound, a trialkylaluminum, a halogenated phenol, a phosphorus compound and a sulfur compound, Catalyst (B) containing a nickel compound, a trialkylaluminum, a fluorinated isopropyl alcohol, a phosphorus compound, a sulfonic acid and water, or Catalyst (C) containing a nickel compound, a trialkylaluminum, a halogenated phenol, a phosphorus compound, a sulfonic acid and water, by which method, the dimer of the lower α-olefin is prepared in a high yield and high selectivity.

20 Claims, No Drawings

DIMERIZATION OF LOW α-OLEFINS

BACKGROUND OF THE INVENTION

1. Field of the Invention

The present invention relates to a process for dimerization of a lower α-olefin, using a nickel-containing catalyst.

2. Description of the Related Art

Dimers of lower α-olefins such as ethylene, propylene, butene, etc. are useful as important raw materials in the production of agricultural chemicals, pharmaceuticals, medicines, perfumes, cosmetics and other chemicals or as monomers of polymers. It is known that the dimers are prepared by dimerizing the lower α-olefin in the presence of a nickel-containing catalyst system. Known nickel-containing catalyst systems for dimerization of the lower α-olefins are, for example, a catalyst system comprising a nickel compound, a trialkylaluminum, a phosphorous compound and a halogenated phenol (cf. Japanese Patent Kokai Publication No. 39004/1979), a catalyst system comprising a nickel compound, a trialkylaluminum, a phosphorous compound, a halogenated phenol and water (cf. Japanese Patent Kokai Publication No. 167932/1982), a catalyst system comprising a nickel compound, a bisdialkylaluminoxane, a phosphorous compound and a halogenated phenol (cf. Japanese Patent Kokai Publication No. 169433/1982) and a catalyst system comprising a nickel compound, a trialkylaluminum, a phosphorous compound and a fluorinated isopropyl alcohol (cf. Japanese Patent Kokai Publication Nos. 158225/1987 and 221335/1989).

SUMMARY OF THE INVENTION

An object of the present invention is to find a nickel-containing catalyst system which effectively catalyzes dimerization of lower α-olefins and to provide a process for preparing the dimers of the lower α-olefins in high yield and with high selectivity.

It has been found that the addition of sulfur compounds such as sulfonic acids, dialkyl sulfates, etc., to the nickel-containing catalyst system improves the yield and the selectivity in dimerization of lower α-olefins.

Accordingly, the present invention provides a process for preparing a dimer of a lower α-olefin comprising dimerizing the α-olefin in the presence of a catalyst system (Catalyst (A)) which comprises:

(1) at least one nickel compound selected from the group consisting of organic acid salts, inorganic acid salts and complex compounds of nickel,
(2) a trialkylaluminum,
(3) at least one compound selected from the group consisting of halogenated phenols of the general formula:

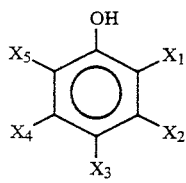

(I)

wherein $X_1$ to $X_5$ independently represent a halogen atom, a hydrogen atom, or a hydroxyl group, with the proviso that at least one of them is a halogen atom, and a fluorinated isopropyl alcohol, (4) at least one phosphorous compound selected from the group consisting of compounds of the formulae:

$$PR^1R^2R^3 \quad (II)$$

$$P(NR^4{}_2)_3 \quad (III)$$

$$P(OR^5)_3 \quad (IV)$$

and $$PR^6R^7(CH_2)_nPR^6R^7 \quad (V)$$

wherein $R^1$, $R^2$, $R^3$, $R^4$, $R^5$, $R^6$ and $R^7$ independently represent an alkyl group, a cycloalkyl group, an aralkyl group or a phenyl group optionally substituted by alkyl groups or alkoxy groups and n is an integer from 1 to 6, and (5) at least one sulfur compound selected from the group consisting of sulfonic acids and dialkyl sulfates; a catalyst system (Catalyst (B)) which comprises:

(1) at least one nickel compound selected from the group consisting of organic acid salts, inorganic acid salts and complex compounds of nickel,
(2) a trialkylaluminum,
(3) a fluorinated isopropyl alcohol,
(4) at least one phosphorous compound selected from the group consisting of compounds of the formulae:

$$PR^1R^2R^3 \quad (II)$$

$$P(NR^4{}_2)_3 \quad (III)$$

$$P(OR^5)_3 \quad (IV)$$

and $$PR^6R^7(CH_2)_nPR^6R^7 \quad (V)$$

wherein $R^1$, $R^2$, $R^3$, $R^4$, $R^5$, $R^6$, $R^7$, and n are the same as defined above, (5) a sulfonic acid, and
(6) water; or a catalyst system (Catalyst (C)) which comprises:

(1) at least one nickel compound selected from the group consisting of organic acid salts, inorganic acid salts and complex compounds of nickel,
(2) a trialkylaluminum;
(3) a halogenated phenol represented by the general formula:

(I)

wherein $X_1$ to $X_5$ are the same as defined above, (4) at least one phosphorous compound selected from the group consisting of compounds of the formulae:

$$PR^1R^2R^3 \quad \text{(II)}$$

$$P(NR^4{}_2)_3 \quad \text{(III)}$$

and $$P(OR^5)_3 \quad \text{(IV)}$$

wherein $R^1$, $R^2$, $R^3$, $R^4$ and $R^5$ are the same as defined above, (5) a sulfonic acid, and
(6) water.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention will be illustrated in details hereinafter.

First, the preparation of Catalyst (A) will be illustrated.

The nickel compounds of the component (1) in Catalyst (A) used in accordance with the present invention include, for example, organic salts such as nickel naphthenate, nickel formate, nickel acetate, nickel benzoate, nickel oxalate, etc.; inorganic salts such as nickel chloride, nickel bromide, nickel iodide, nickel fluoride, nickel nitrate, nickel sulfate, etc.; and complex compounds of nickel such as nickel bis-(acetylacetonate), nickel bis-(ethylacetoacetate), nickel bis-(dimethylglyoximate), etc. Two or more nickel compounds may be used in combination.

The trialkylaluminums of the component (2) in Catalyst (A) include, for example, trimethylaluminum, triethylaluminum, tri-n-propylaluminum, tri-isopropylaluminum, tri-n-butylaluminum, tri-isobutylaluminum, tri-n-pentyaluminum, tri-n-hexylaluminum, tricyclohexylaluminum, etc.

Amount of the trialkylaluminum is usually 2–500 moles, preferably 2–100 moles, more preferably 2–50 moles per mole of the nickel compound.

The halogenated phenols of the component (3) in Catalyst (A) which are represented by the formula (I) include, for example, o-, m- and p-chlorophenol, 2,3-, 2,4-, 2,5-, 2,6-, 3,4- and 3,5-dichlorophenol, 2,4,5,- and 2,4,6-trichlorophenol, 2,3,4,6-tetrachlorophenol, pentachlorophenol, 2,3-dichlorohydroquinone, 2,6-dichlorohydroquinone, tetrachlorohydroquinone, 4,6-dichlororesorcine, 2,4,6-trichlororesorcine and tetrachlorocatechol and halogenated phenols in which the chlorine atoms in the compounds mentioned above are substituted by at least one fluorine, bromine or iodine atom.

The amount of the halogenated phenol is usually 0.4–20 moles, preferably 1–10 moles per mole of the trialkylaluminum.

The fluorinated isopropyl alcohols of the component (3) in Catalyst (A) include, for example, 1,1,3,3-tetrafluoroisopropyl alcohol, 1,1,1,3-tetrafluoroisopropyl alcohol, 1,1,1,3,3-pentafluoroisopropyl alcohol, 1,1,1,3,3,3-hexafluoroisopropyl alcohol, etc. Among them, 1,1,1,3,3,3-hexafluoroisopropyl alcohol is particularly preferred.

The amount of the fluorinated isopropyl alcohol is usually 0.2–10 moles, preferably 0.5–5 moles per mole of the trialkylaluminum.

The amount of the halogenated phenol or the fluorinated isopropyl alcohol used has a relationship to the composition of the dimers produced. For example, in the case of the dimerization of propylene, the selectivity of 2,3-dimethyl-2-butene produced tends to increase with the increase of the amount of the halogenated phenol or the fluorinated isopropyl alcohol.

The phosphorous compounds of the component (4) in Catalyst (A) include, for example, the phosphines represented by the formula [II] such as trimethylphosphine, triethylphosphine, tri-n-propylphosphine, triisopropylphosphine, tri-n-butylphosphine, triisobutylphosphine, tri-tert-butylphosphine, tri-sec-butylphosphine, tricyclopropylphosphine, tricyclohexylphosphine, triphenylphosphine, tri-p-tolylphosphine, tri-p-methoxyphenylphosphine, tri-2,4,6-trimethylphenylphosphine, phenyl-diisopropylphosphine, diethylisopropylphosphine, ethyl-di-tert-butylphosphine, diethyl-tert-butylphosphine, ethyldicyclohexylphosphine, methylphenylbenzylphosphine, diethylphenylphosphine, ethyldiphenylphosphine, dimethylphenylphosphine, methyldiphenylphosphine, diisopropyl-ethylphosphine etc.; the aminophosphines represented by the formula [III] such as trisdimethylaminophosphine, trisdiethylaminophosphine, trisdi-n-propylaminophosphine, trisdiisopropylaminophosphine, trisdi-n-butylaminophosphine, trisdiisobutylaminophosphine, trisdi-tert-butylaminophosphine, trisdicyclohexylaminophosphine, etc.; the phosphites represented by the formula [IV] such as trimethylphosphite, triethylphosphite, tri-n-propylphosphite, triisopropylphosphite, tri-n-butylphosphite, triisobutylphosphite, tri-tert-butylphosphite, tricyclohexylphosphite, triphenylphosphite, tri-p-tolylphosphite, tri-p-methoxyphenylphosphite, etc.; and the bidentate phosphines represented by the formula [V] such as bisdiphenylphosphinomethane, 1,2-bis(diphenylphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane, 1,2-bis(dimethylphosphino)ethane, 1,2-bis(diethylphosphino)ethane, 1,2-(diethylphosphino)ethane, 1,2-bis(dicyclohexylphosphino)ethane, 1,2-bis(dipentafluorophenylphosphino)ethane, etc.

There is a relationship between the kind of the phosphorous compound used and the composition of the dimers produced. For example, in the case of the dimerization of propylene, the use of a phosphine such as triisopropylphosphine, tricyclohexylphosphine, tri-sec-butylphosphine, ethyl-di-tert-butylphosphine, and the like provides predominantly 2,3-dimethylbutenes, while the use of the bidentate phosphine, such as 1,2-bis(diphenylphosphino)ethane, provides predominantly methylpentenes.

The amount of the phosphorous compound is usually 0.1–50 moles, preferably 0.1–20 moles, more preferably 0.1–2 moles per mole of the nickel compound.

As the sulfur compound of the component (5) in Catalyst (A), there is used at least one compound selected from sulfonic acids and dialkyl sulfates. The sulfonic acids include, for example, aliphatic sulfonic acids such as methanesulfonic acid and ethanesulfonic acid; aromatic sulfonic acids such as benzenesulfonic acid, p-toluenesulfonic acid and ethylbenzenesulfonic acid; and halogen-containing sulfonic acid such as chlorosulfonic acid and trifluoromethanesulfonic acid. The dialkyl sulfates include, for example, dimethyl sulfate and diethyl sulfate. These sulfur compounds may be used in admixture of two or more compounds. Particularly, the combined use of the sulfonic acids and the dialkyl sulfates provides an increased activity and selectivity of the catalyst for the dimerization of the lower α-olefin.

The amount of the sulfur compound is usually 0.1–20 moles, preferably 0.1–10 moles per mole of the nickel compound.

The catalyst according to the invention is usually prepared in the presence of an inert solvent. The inert solvents include, for example, aromatic hydrocarbons such as benzene, toluene, xylene, etc.; aliphatic hydrocarbons such as hexane, heptane, cyclohexane, etc.; and halogenated hydrocarbons such as dichloromethane, dichloroethane, chlorobenzene, dichlorobenzene, etc.

In the preparation of the catalysts, the order of addition of the components is not specified, but any order may be applicable. Especially, the catalysts of high stability are preferably prepared in the presence of a conjugated diene such as butadiene, isoprene, 1,2-pentadiene and 2,3-dimethyl-1,3-butadiene. If the conjugated diene is present in an excess amount, the dimerization of the lower α-olefin is prevented. Therefore, a molar amount of the conjugated diene is preferably from 1 to 200 times the amount the nickel compound.

The catalyst may usually be prepared at a temperature of $-78$ to $100°$ C., preferably $-50$ to $30°$ C.

The preparation of Catalyst (B) will be also illustrated as follows:

The nickel compounds of the component (1) in Catalyst (B) are the same as those in Catalyst (A).

The trialkylaluminums of the component (2) in Catalyst (B) are also the same as those in Catalyst (A) and are used in similar amounts to those in Catalyst (A).

The fluorinated isopropyl alcohols of the component (3) in Catalyst (B) are the same as those in Catalyst (A) and are also used in similar amounts to those in Catalyst (A).

There is a relationship between the amount of the fluorinated isopropyl alcohol used and the composition of the dimers produced. For example, in the case of the dimerization of propylene, the increased amount of the fluorinated isopropyl alcohol leads to the increase in the selectivity of 2,3-dimethyl-2-butene produced.

The phosphorous compounds of the component (4) in Catalyst (B) are the same as those in Catalyst (A) and used in similar amounts to those in Catalyst (A).

There is a relationship between the kind of the phosphorous compound used and the composition of the dimers produced. For example, when propylene is dimerized, the use of the phosphines such as trisopropylphosphine, tricyclohexylphosphine, tri-sec-butylphosphine or ethyl-di-tert-butylphosphine provides predominantly 2,3-dimethylbutenes, while the use of the bidentate phosphines such as 1,2-bisdiphenylphosphinoethane gives predominantly methylpentenes.

The sulfonic acids of the component (5) in Catalyst (B) are the same as those in Catalyst (A), and used in similar amounts to those in Catalyst (A).

The amount of water of the catalyst component (6) in Catalyst (B) is usually 0.1–10 moles, preferably from 1 to 5 moles per mole of the nickel compound, and is usually 0.1–2 moles, preferably 0.2–1 moles per mole of the trialkylaluminum.

Catalyst (B) can be prepared under the similar conditions to those employed in the preparation of Catalyst (A).

Finally the preparation of Catalyst (C) will be illustrated as follows.

The nickel compounds of the component (1) in Catalyst (C) are the same as those in Catalyst (A).

The trialkylaluminums of the component (2) in Catalyst (C) are also the same as those in Catalyst (A), and are used in similar amounts to those in Catalyst (A), The halogenated phenols of the component (3) in Catalyst (C) are the same as those in Catalyst (A) and are used in similar amounts to those in Catalyst (A)

The phosphines of the formula (II), the aminophosphines of the formula (III) and the phosphites of the formula (IV) which are used as the component (3) in Catalyst (C) are the same as those in Catalyst (A) and are used in similar amounts to those in Catalyst (A).

There is a relation between the kind of the phosphorous compound used and the composition of the dimers produced. For example, in the dimerization of propylene, the use of a phosphine such as triisopropylphosphine, tricyclophosphine, tri-sec-butylphosphine, ethyl-di-tert-butylphosphine provides predominantly 2,3-dimethylbutenes.

The sulfonic acids of the component (5) in Catalyst (C) are the same as those in Catalyst (A) and are used in similar amounts to those in Catalyst (A).

The water of component (6) in Catalyst (C) is used in a similar amount to that in Catalyst (A).

Catalyst (C) can be prepared under the similar conditions to those employed in the preparation of Catalyst (A).

The dimerization of the lower α-olefin can be carried out in the inert solvent described above, using either of Catalyst (A), Catalyst (B) and Catalyst (C) in an amount of $10^{-5}$ to $10^{-1}$ mol/liter in terms of the concentration of the nickel component.

A dimerization temperature is usually from $-70°$ to $150°$ C., preferably from $-50°$ to $100°$ C., more preferably from $-20°$ to $50°$ C., and dimerization pressure is usually from 0 to 30 Kg/cm$^2$G.

The lower α-olefins to be dimerized by the process of the present invention include, for example, ethylene, propylene, 1-butene, 1-pentene, 3-methyl-1-butene, 1-hexene, 3-methyl-1-pentene, 4-methyl-1-pentene, 3,3-dimethyl-1-butene and the like. Among them, ethylene, propylene and 1-butene are preferably used.

After the reaction is completed, the product can be isolated by stopping the reaction in a per se conventional manner, removing the catalyst, and distillating the residue. The desired dimer is thereby obtained. According to the present invention, the dimer of the lower α-olefin can be obtained in a high yield and with high selectivity.

PREFERRED EMBODIMENTS OF THE INVENTION

The invention will be illustrated by the following examples, which, however, limit the present invention in no way.

Examples 1 and 2

In a 50 ml Schlenk-type tube which had been cooled to 5° C. and filled with nitrogen, 1.35 ml of toluene containing 0.1 mmol of nickel naphthenate, 0.1 mmol of tricyclohexylphosphine (in 20% toluene solution) and 8 mmol of isoprene were charged at 5° C., followed by the addition of 2 ml of toluene containing 2 mmol of triethylaluminum. The mixture was heated to 18° C. with stirring.

Then the mixture was cooled to 5° C. and methanesulfonic acid was added thereto in an amount shown in Table 1. Further 3.5 ml of toluene containing 3.5 mmol of 2,4,6-trichlorophenol was added in such manner that the internal temperature in the tube did not exceed 20° C.

In a stainless steel 500 ml autoclave which had been filled with nitrogen, the catalyst solution which had been prepared as described above and 18 ml of toluene were added at 20° C. and then propylene was injected to a pressure of 4 Kg/cm$^2$G to react at 20° C. for 3 hours.

After the reaction was completed, the reaction mixture was cooled to 5° C., followed by purging of unreacted propylene from the mixture. Then the reaction mixture was analyzed by gas chromatography. The results are shown in Table 1.

TON(turnover number)=the amount of the dimers produced (mmol)/ the amount of the nickel metal used (mmol)

Selectivity of dimer (%)=[the amount of the dimers produced (g)/ the amount of the propylene reacted (g)]×100

Dimers: DMB-1+DMB-2+2M1P+2M2P+4M1,2P+Hex (DMB-1: 2,3-dimethyl-1-butene, DMB-2: 2,3-dimethyl-2-butene, 2M1P: 2-methyl-1-pentene, 2M2P: 2-methyl-2-pentene, 4M1,2P: 4-methyl-1-pentene+4-methyl-2-pentene, Hex: Hexene)

Comparative Example 1

Example 1 was repeated except that 0.8 mmol of water was used in place of methanesulfonic acid. The results are given in Table 1.

TABLE 1

| | Methanesulfonic acid/Ni (molar ratio) | Selectivity of dimers (%) | TON Total dimers | DMB-1 + DMB-2 |
|---|---|---|---|---|
| Example 1 | 3 | 75 | 8,786 | 7,046 |
| Example 2 | 5 | 77 | 11,021 | 8,784 |
| Comp. Exam. 1[1)] | — | 62 | 6,856 | 5,862 |

[1)]Water/Nickel (molar ratio) = 8

Example 3

Example 1 was repeated except that 0.1 mmol of trifluoromethanesulfonic acid was used in place of methanesulfonic acid and that the reaction was carried out for 2 hours. The selectivity of the dimers was 90.1%, and the TON of the total dimers and DMB-1+DMB-2 were 17,080 and 8,400, respectively.

Example 4

Example 3 was repeated except that the reaction was carried out at a temperature of 10° C. for 1 hour. After the reaction was completed, the reaction mixture was analyzed by gas chromatography. The selectivity of the dimers was found to be 94.6%, and the TON of the total dimers and DMB-1+DMB-2 to be 28,830 and 17,696, respectively.

Example 5

Example 4 was repeated except that 0.02 mmol of nickel naphthenate, 0.02 mmol of tricyclohexylphosphine, 0.02 ml of trifluoromethanesulfonic acid, 0.16 mmol of isoprene, 0.40 mmol of triethylaluminum and 0.70 mmol of 2,4,6-trichlorophenol were used. After the reaction was completed, the reaction mixture was analyzed by gas chromatography. The selectivity of the dimers was found to be 99.4%, and the TON of the total dimers and DMB-1+DMB-2 to be 70,906 and 39,227, respectively.

Example 6

Example 5 was repeated except that the reaction was carried out at a pressure of 6 Kg/cm$^2$ for 40 minutes. After the reaction was completed, the reaction mixture was analyzed by gas chromatography. The selectivity of the dimers was found to be 94.1%, and the TON of the total dimers and DMB-1+DMB-2 to be 112,778 and 51,495, respectively.

Example 7

Into a 50 ml Schlenk-type tube which had been cooled to 5° C. and filled with nitrogen, 0.375 ml toluene containing 0.01 mmol of nickel naphthenate, 0.01 mmol of tricyclohexylphosphine (in 20% toluene solution) and 0.8 mmol of isoprene were charged at 5° C., followed by the addition of 0.2 ml of toluene containing 0.2 mmol of triethylaluminum. The mixture was heated to 18° C. with stirring.

Then the mixture was cooled to 5° C. and 0.02 mmol of dimethyl sulfate was added thereto. Further, 0.7 ml of toluene containing 0.7 mmol of 2,4,6-trichlorophenol was added in such manner that the internal temperature in the tube did not exceed 20° C.

In a stainless steel 100 ml autoclave which had been filled with nitrogen, the catalyst solution which had been prepared as described above and 2 ml of toluene were added at 15° C. and propylene was injected to a pressure of 6 Kg/cm$^2$G to react at 15° C. to 20° C. for 1 hour.

After the reaction was completed, the reaction mixture was cooled to 5° C., followed by purging unreacted propylene from the mixture. Then it was analyzed by gas chromatography. The results are given in Table 2.

Example 8

Example 7 was repeated except that dimethyl sulfate was used in an amount of 0.03 mmol. The results are given in Table 2.

Example 9

Example 7 was repeated except that o-dichlorobenzene was used in place of toluene and that dimethyl sulfate was used in an amount of 0.04 mmol. The results are given in Table 2.

Example 10

Example 7 was repeated except that diethyl sulfate was used in an amount of 0.03 mmol in place of dimethyl sulfate. The results are given in Table 2.

TABLE 2

| | Selectivity of dimers (%) | TON Total dimers | DMB-1 | DMB-2 |
|---|---|---|---|---|
| Example 7 | 64 | 28,339 | 17,496 | 4,420 |
| Example 8 | 68 | 29,552 | 17,295 | 4,337 |
| Example 9 | 64 | 30,514 | 18,606 | 4,341 |
| Example 10 | 72 | 21,335 | 14,144 | 2,177 |

Example 11

In a 50 ml Schlenk-type tube which had been cooled to 5° C. and filled with nitrogen, 0.68 ml of toluene containing 0.05mmol of nickel naphthenate, 0.05 mmol of tricyclohexylphosphine (in 20% toluene solution) and 4 mmol of isoprene were charged at 5° C., followed by the addition of 1 ml of toluene containing 1 mmol of triethylaluminum. The mixture was heated to 18° C. with stirring.

Then the mixture was cooled to 5° C. and 0.15 mmol of dimethyl sulfate was added thereto. Further 3.5 ml of toluene containing 3.5 mmol of 2,4,6-trichlorophenol was added in such manner that the internal temperature in the tube did not exceed 20° C.

In a stainless steel 500 ml autoclave which had been filled with nitrogen, the catalyst solution prepared as described above and 18 ml of toluene were introduced at 15° C. and then propylene was injected to a pressure of 4 Kg/cm$^2$G to react at 20° C. for 2 hours.

After the reaction was completed, the reaction mixture was cooled to 5° C., followed by purging unreacted propylene from the mixture. Then it was analyzed by gas chromatography. The results are given in Table 3.

Example 12

Example 11 was repeated except that triethylaluminum was used in an amount of 0.75 mmol, dimethyl sulfate in an amount of 0.115 mmol and 2,4,6-trichlorophenol in an amount of 2.5 mmol. The results are given in Table 3.

TABLE 3

|  | Selectivity of dimers (%) | TON Total dimers | DMB-1 | DMB-2 |
| --- | --- | --- | --- | --- |
| Example 11 | 68 | 18,121 | 2,156 | 11,852 |
| Example 12 | 68 | 16,349 | 11,011 | 1,921 |

Example 13

In a 50 ml Schlenk-type tube which had been cooled to 5° C. and filled with nitrogen, 0.375 ml of toluene containing 0.01 mmol of nickel naphthenate, 0.01 mmol of triisopropylphosphine and 0.8 mmol of isoprene were charged at the same temperature, followed by the addition of 0.15 ml of toluene containing 0.15 mmol of triethylaluminum. The mixture was heated to 18° C. with stirring.

Then the mixture was cooled to 5° C. and was added 0.025 mmol of dimethyl sulfate thereto. Further, 0.5 ml of toluene containing 0.5 mmol of 2,4,6-trichlorophenol was added in such manner that the internal temperature in the tube did not exceed 20° C.

In a stainless steel 100 ml autoclave which had been filled with nitrogen, the catalyst solution prepared as described above and 2 ml of toluene were introduced at 15° C. and then propylene was injected to a pressure of 6 Kg/cm$^2$G to react at a temperature of 15° C. to 20° C. for 1 hour.

After the reaction was completed, the reaction mixture was cooled to 5° C., followed by purging unreacted propylene from the mixture. Then it was analyzed by gas chromatography. The results are given in Table 4.

Example 14

Example 13 was repeated except that 0.01 mmol of triethylphosphine was used in place of triisopropylphosphine. The results are given in Table 4.

Example 15

Example 13 was repeated except that 0.01 mmol of diethylphenylphosphine was used in place of triisopropylphosphine. The results are given in Table 4.

TABLE 4

|  | Selectivity of dimers (%) | TON Total dimers | DMB-1 | DMB-2 | 2M1P | 2M2P | 4M1,2P |
| --- | --- | --- | --- | --- | --- | --- | --- |
| Example 13 | 64 | 11,484 | 7,763 | 1,088 | 1,072 | 393 | 1,064 |
| Example 14 | 90 | 16,821 | 4,499 | 169 | 2,469 | 4,151 | 4,971 |
| Example 15 | 87 | 9,618 | 2,424 | 263 | 1,903 | 2,503 | 2,525 |

Example 16

In a 50 ml Schlenk-type tube which had been cooled to 5° C. and filled with nitrogen, 0.68 ml of toluene containing 0.05 mmol of nickel naphthenate, 0.05 mmol of tricyclohexylphosphine (in 20% toluene solution) and 4 mmol of isoprene were charged at 5° C., followed by the addition of 0.9 ml of toluene containing 1 mmol of triethylaluminum. The mixture was heated to 18° C. with stirring.

Then the mixture was cooled to 5° C. and 0.09 mmol of dimethyl sulfate was added thereto. Further, 2.5 ml of toluene containing 2.5 mmol of 2,4,6-trichlorophenol was added in such manner that the internal temperature in the tube did not exceed 20° C.

In a stainless steel 500ml autoclave which had been filled with nitrogen, the catalyst solution prepared as described above and 18 ml of toluene were introduced at 15° C. and then propylene was injected to a pressure of 4 Kg/cm$^2$G to react at 20° C. for 2 hours.

After the reaction was completed, the reaction mixture was cooled to 5° C., followed by purging unreacted propylene from the mixture. Then it was analyzed by gas chromatography. The results are given in Table 3.

Example 17

Example 16 was repeated except that 0.125 mmol of methanesulfonic acid was further added after the addition of 0.09 mmol of diethyl sulfate. The results are given in Table 5.

Example 18

Example 16 was repeated except that 0.15 mmol of methanesulfonic acid was further added after the addition of 0.09 mmol of diethyl sulfate. The results are given in Table 5.

Example 19

Example 16 was repeated except that 0.2 mmol of methanesulfonic acid was further added after the addition of 0.09 mmol of diethyl sulfate. The results are given in Table 5.

TABLE 5

|  | Selectivity of dimers (%) | TON Total dimers | DMB-1 | DMB-2 |
| --- | --- | --- | --- | --- |
| Example 16 | 66.9 | 9,399 | 4,993 | 2,028 |

TABLE 5-continued

|  | Selectivity of dimers (%) | TON | | |
|---|---|---|---|---|
|  |  | Total dimers | DMB-1 | DMB-2 |
| Example 17 | 70.4 | 24,124 | 16,195 | 2,742 |
| Example 18 | 77.5 | 28,822 | 20,631 | 2,138 |
| Example 19 | 76.5 | 23,760 | 16,751 | 2,043 |

Example 20

In a 50 ml Schlenk-type tube which had been cooled to 5° C. and filled with nitrogen, 1.24 ml of toluene containing 0.1 mmol of nickel naphthenate, 0.1 mmol of 1,2-bis(diphenylphosphino)ethane and 8 mmol of isoprene were charged at 5° C., followed by the addition of 2 ml of toluene containing 2 mmol of triethylaluminum.

Then 0.3 mmol of trifluoromethanesulfonic acid was added at 5° C. and further 3.5 ml of toluene containing 3.5 mmol of 2,4,6-trichlorophenol was added in such manner that the internal temperature in the tube did not exceed 20° C.

In a stainless steel 500 ml autoclave which had been filled with nitrogen, the catalyst solution prepared as described above and 12 ml of toluene were introduced at 10° C. and then propylene was injected to a pressure of 4.5 Kg/cm2G to react at the same temperature for 2 hours.

After the reaction was completed, the reaction mixture was cooled to 0° C., followed by purging unreacted propylene from the mixture. Then it was analyzed by gas chromatography. The results are given in Table 6.

Example 21

Example 20 was repeated except that 0.1 mmol of 1,6-bis(diphenylphosphino)hexane was used in place of 1,2-bis(diphenylphosphino)ethane. The results are given in Table 6.

TABLE 6

|  | Selectivity of dimers (%) | TON | | |
|---|---|---|---|---|
|  |  | Total dimers | 4M1,2P | Methylpentenes |
| Example 20 | 97.8 | 8,110 | 4,480 | 7,650 |
| Example 21 | 100 | 26,600 | 9,120 | 15,140 |

Example 22

In a 50 ml Schlenk-type tube which had been cooled to 5° C. and filled with nitrogen, 0.375 ml of toluene containing 0.01 mmol of nickel naphthenate, 0.01 mmol of tricyclohexylphosphine (in 20% toluene solution) and 0.8 mmol of isoprene were charged at 5° C., followed by the addition of 0.2 ml of toluene containing 0.2 mmol of triethylaluminum. The mixture was heated to 18° C. with stirring.

Then the mixture was cooled to 5° C. and 0.025 mmol of dimethyl sulfate was added thereto. Further, 0.3 ml of toluene containing 0.3 mmol of 1,1,1,3,3,3-hexafluoroisopropyl alcohol was added in such manner that the internal temperature in the tube did not exceed 20° C.

In a stainless steel 100ml autoclave which had been filled with nitrogen, the catalyst solution prepared as described above and 2 ml of toluene were introduced at 15° C. and then propylene was injected to a pressure of 6 Kg/cm²G to react at 20° C. for 1 hour.

After the reaction was completed, the reaction mixture was cooled to 5° C., followed by purging unreacted propylene from the mixture. Then it was analyzed by gas chromatography. The results are given in Table 7.

Example 23

Example 22 was repeated except that 0.07 mmol of methanesulfonic acid was used in place of dimethyl sulfate. The results are given in Table 7.

Example 24

Example 22 was repeated except that 0.1 mmol of triethylaluminum and 0.15 mmol of 1,1,1,3,3,3-hexafluoroisopropyl alcohol were used and that 0.01 mmol of trifluoromethanesulfonic acid was used in place of dimethyl sulfate. The results are given in Table 7.

Example 25

Example 22 was repeated except that 0.15 mmol of triethylaluminum was used. The results are given in Table 7.

Example 26

Example 22 was repeated except that 0.4 mmol of 1,1,1,3,3,3-hexafluoroisopropyl alcohol was used. The results are given in Table 7.

Example 27

Example 24 was repeated except that 0.02 mmol of chlorosulfonic acid was used in place of trifluoromethanesulfonic acid. The results are given in Table 7.

Comparative Example 2

Example 22 was repeated except that 0.02 mmol of nickel naphthenate, 0.02 mmol of tricyclohexylphosphine, 1.6 mmol of isoprene were and 0.60 mmol of 1,1,1,3,3,3-hexafluoroisopropyl alcohol used, and that dimethyl sulfate was not used. The results are given in Table 7.

Comparative Example 3

Example 22 was repeated except that 0.02 mmol of nickel naphthenate, 0.02 mmol of tricyclohexylphosphine, 1.6 mmol of isoprene and 0.15 mmol of 1,1,1,3,3,3-hexafluoroisopropyl alcohol were used, and no dimethyl sulfate was used. The results are given in Table 7.

TABLE 7

|  | Selectivity of dimers (%) | TON | | |
|---|---|---|---|---|
|  |  | Total dimers | DMB-1 | DMB-2 |
| Example 22 | 43 | 9,322 | 7,679 | 562 |
| Example 23 | 50 | 15,407 | 7,226 | 6,163 |
| Example 24 | 65 | 17,317 | 13,903 | 62 |
| Example 25 | 44 | 11,881 | 2,337 | 7,786 |
| Example 26 | 53 | 17,607 | 1,265 | 13,560 |
| Example 27 | 97 | 8,210 | 6,041 | 8 |
| Comp. Exam. 2 | 37 | 4,149 | 283 | 3,339 |
| Comp. Exam. 3 | 34 | 2,466 | 2,184 | 50 |

Example 28

In a 50 ml Schlenk-type tube which had been cooled to 5° C. and filled with nitrogen, 1.35 ml of toluene containing 0.1 mmol of nickel naphthenate, 0.1 mmol of tricyclohexylphosphine (in 20% toluene solution) and 0.8 mmol of isoprene were charged at 5° C., followed by the addition of 1 ml of toluene containing 1 mmol of triethylaluminum. The mixture was heated to 18° C. with stirring.

Then the mixture was cooled to −5° C. and 0.1 mmol of trifluoromethanesulfonic acid was added thereto. Further, 1.5 ml of toluene containing 1.5 mmol of 1,1,1,3,3,3-hexafluoroisopropanol was added in such manner that the internal temperature in the tube did not exceed 20° C.

In a stainless steel 500 ml autoclave which had been filled with nitrogen, the catalyst solution prepared as described above and 18 ml of toluene were introduced at 15° C. and then propylene was injected to a pressure of 4 Kg/cm$^2$G to react at 20° C. for 2 hours.

After the reaction was completed, the reaction mixture was cooled to 5° C., followed by purging of unreacted propylene from the mixture. Then the reaction mixture was analyzed by gas chromatography. The results are given in Table 8.

Example 29

Example 28 was repeated except that 0.05 mmol of trifluoromethanesulfonic acid was used. The results are given in Table 8.

Example 30

Example 28 was repeated except that 0.05 mmol of nickel naphthenate, 0.05 mmol of tricyclohexylphosphine, 4 mmol of isoprene, 0.5 mmol of triethylaluminum and 0.75 mmol of 1,1,1,3,3,3-hexafluoroisopropyl alcohol were used, and that 0.075 mmol of trifluoromethanesulfonic acid and 0.05 mmol of dimethyl sulfate were used in place of 0.1 mmol of trifluoromethanesulfonic acid. The results are given in Table 8.

Example 31

Example 28 was repeated except that 0.05 mmol of nickel naphthenate, 0.05 mmol of tricyclohexylphosphine, 4 mmol of isoprene, 0.5 mmol of triethylaluminum and 0.75 mmol of 1,1,1,3,3,3-hexafluoroisopropyl were used, and that 0.125 mmol of trifluoromethanesulfonic acid and 0.05 mmol of dimethyl sulfate were used in place of 0.1 mmol of trifluoromethanesulfonic acid. The results are given in Table 8.

Example 32

Example 28 was repeated except that 0.05 mmol of nickel naphthenate, 0.05 mmol of tricyclohexylphosphine, 4 mmol of isoprene, 0.5 mmol of triethylaluminum and 0.75 mmol of 1,1,1,3,3,3-hexafluoroisopropyl alcohol were used and that 0.125 mmol of trifluoromethanesulfonic acid and 0.05 mmol of diethyl sulfate were used in place of 0.1 mmol of trifluoromethanesulfonic acid. The results are given in Table 8.

Example 33

Example 24 was repeated except that 0.01 mmol of triisopropylphosphine was used in place of tricyclohexylphosphine. The results are given in Table 9.

Example 34

Example 24 was repeated except that 0.01 mmol of triethylphosphine was used in place of tricyclohexylphosphine. The results are given in Table 9.

Example 35

Example 24 was repeated except that 0.01 mmol of diethylphenylphosphine was used in place of tricyclohexylphosphine. The results are given in Table 9.

TABLE 8

|  | Selectivity of dimers (%) | TON | | |
|---|---|---|---|---|
|  |  | Total dimers | DMB-1 | DMB-1 + DMB-2 |
| Example 28 | 83.9 | 19,179 | 14,937 | 15,081 |

TABLE 8-continued

|  | Selectivity of dimers (%) | TON | | |
|---|---|---|---|---|
|  |  | Total dimers | DMB-1 | DMB-1 + DMB-2 |
| Example 29 | 78.9 | 13,119 | 10,182 | 10,988 |
| Example 30 | 86.2 | 25,290 | 19,007 | 19,646 |
| Example 31 | 84 | 26,332 | 20,087 | 20,241 |
| Example 32 | 86.2 | 23,983 | 18,044 | 18,218 |

TABLE 9

|  | Selectivity of dimers (%) | TON | | | | | |
|---|---|---|---|---|---|---|---|
|  |  | Total dimers | DMB-1 | DMB-2 | 2M1P | 2M2P | 4M1,2P |
| Example 24 | 65 | 17,317 | 13,903 | 62 | 1,874 | 166 | 1,136 |
| Example 33 | 76.3 | 16,544 | 12,210 | 33 | 1,754 | 165 | 2,200 |
| Example 34 | 89.3 | 14,661 | 5,665 | 146 | 3,596 | 2,715 | 2,304 |
| Example 35 | 92 | 20,872 | 5,560 | 272 | 4,701 | 5,223 | 4,053 |

Example 36

Example 28 was repeated except that 0.12 ml of toluene containing 0.1 mmol of nickel naphthenate and 0.1 mmol of tri-sec-butylphosphine were used, and that the reaction was carried out at a temperature of 10° C. for 1 hour. The results are given in Table 10.

Example 37

Example 36 was repeated except that 0.06 ml of toluene containing 0.05 mmol of nickel naphthenate, 0.05 mmol of diisopropylethylphosphine, 4 mmol of isoprene, 0.5 mmol of triethylaluminum, 0.05 mmol of trifluoromethanesulfonic acid and 0.75 mmol of 1,1,1,3,3,3-hexafluoroisopropyl alcohol were used. The results are given in Table 10.

Example 38

Example 37 was repeated except that 0.05 mmol of triisopropylphosphine was used in place of diisopropylethylphosphine. The results are given in Table 10.

Example 39

Example 36 was repeated except that 0.10 mmol of triisopropylphosphine was used in place of tri-sec-butylphosphine and that 0.08 mmol of trifluoromethanesulfonic acid was used. The results are given in Table 10.

TABLE 10

|  | Selectivity of dimers (%) | TON | | |
|---|---|---|---|---|
|  |  | Total dimers | DMB-1 | DMB-1 + DMB-2 |
| Example 36 | 80.9 | 22,694 | 17,454 | 17,500 |

TABLE 10-continued

| | Selectivity of dimers (%) | TON | | |
|---|---|---|---|---|
| | | Total dimers | DMB-1 | DMB-1 + DMB-2 |
| Example 37 | 85.9 | 49,807 | 27,397 | 27,566 |
| Example 38 | 94.5 | 34,878 | 26,625 | 26,753 |
| Example 39 | 85.5 | 28,006 | 14,618 | 14,755 |

Example 40

In a 50 ml Schlenk-type tube which had been cooled to 5° C. and filled with nitrogen, 1.35 ml of toluene containing 0.1 mmol of nickel naphthenate, 0.1 mmol of tricyclohexylphosphine (in 20% toluene solution) and 8 mmol of isoprene were charged at 5° C., followed by the addition of 1 ml of toluene containing 1 mmol of triethylaluminum. The mixture was heated to 18° C. with stirring.

Then the mixture was cooled to 5° C. and 0.1 mmol of trifluoromethanesulfonic acid was added thereto. Then 1.5 ml of toluene containing 1.5 mmol of 1,1,1,3,3,3-hexafluoroisopropyl alcohol was added in such manner that the internal temperature in the tube did not exceed 20° C.

In a stainless steel 1,500ml autoclave which had been filled with nitrogen, the catalyst solution prepared as described above and 40 ml of toluene were introduced at 15° C. and then propylene was injected to a pressure of 3 Kg/cm$^2$G to react at 10° C. for 2 hours.

After the reaction was completed, the reaction mixture was cooled to 5° C., followed by purging unreacted propylene from the mixture. Then it was analyzed by gas chromatography. The results are given in Table 10.

Example 41

In the same manner as in Example 40 except that 0.15 mmol of nickel naphthenate, 0.15 mmol of tricyclohexylphosphine, 12 mmol of isoprene, 1.5 mmol of triethylaluminum, 0.15 mmol of trifluoromethanesulfonic acid and 2.25 mmol of 1,1,1,3,3,3-hexafluoroisopropyl alcohol were used, the catalyst was prepared.

In a stainless steel 1,500 ml autoclave which had been filled with nitrogen, one third of the catalyst prepared as described above and 36 ml of toluene were introduced at 15° C. and then propylene was injected to a pressure of 3 Kg/cm$^2$G to start the reaction at 10° C. The remaining catalyst solution was divided into two portions and added to the reaction mixture after 1 and 2 hours from the start of the reaction respectively, and the reaction was continued for additional 1 hour.

After the reaction was completed, the reaction mixture was cooled to 5° C., followed by purging unreacted propylene from the mixture. Then it was analyzed by gas chromatography. The results are given in Table 11.

Example 42

Example 41 was repeated except that propylene was injected to a pressure of 4 Kg/cm$^2$G. The results are given in Table 11.

TABLE 11

| | Selectivity of dimers (%) | TON | | |
|---|---|---|---|---|
| | | Total dimers | DMB-1 | DMB-1 + DMB-2 |
| Example 40 | 74.5 | 48,737 | 38,210 | 38,210 |
| Example 41 | 83.1 | 45,009 | 35,487 | 35,737 |

TABLE 11-continued

| | Selectivity of dimers (%) | TON | | |
|---|---|---|---|---|
| | | Total dimers | DMB-1 | DMB-1 + DMB-2 |
| Example 42 | 78.3 | 56,209 | 42,700 | 43,843 |

Example 43

In a 50 ml Schlenk-type tube which had been cooled to 5° C. and filled with nitrogen, 1.2 ml of toluene containing 0.05 mmol of nickel naphthenate, 0.05 mmol of 1,2-bis(diphenylphosphino)ethane and 4 mmol of isoprene were charged at 5° C., followed by the addition of 0.5 ml of toluene containing 0.5 mmol of triethylaluminum. The mixture was heated to 18° C. with stirring.

Then the mixture was cooled to 5° C. and 0.1 mmol of trifluoromethanesulfonic acid was added thereto. Further, 0.75 ml of toluene containing 0.75 mmol of 1,1,1,3,3,3-hexafluoroisopropyl alcohol was added in such manner that the internal temperature in the tube did not exceed 20° C.

In a stainless steel 500 ml autoclave which had been filled with nitrogen, the catalyst solution prepared as described above and 18 ml of toluene were introduced at 15° C. and then propylene was injected to a pressure of 4 Kg/cm$^2$G to react at 20° C. for 2 hours.

After the reaction was completed, the reaction mixture was cooled to 5° C., followed by purging unreacted propylene from the mixture. Then it was analyzed by gas chromatography. The results are given in Table 12.

Example 44

Example 43 was repeated except that 0.05 mmol of bisdiphenylphosphinomethane was used in place of 1,2-bis(diphenylphosphino)ethane. The results are given in Table 12.

Example 45

Example 43 was repeated except that 0.05 mmol of 1,6-bis(diphenylphosphino)hexane was used in place of 1,2-bis(diphenylphosphino)ethane, and that 0.05 mmol of trifluoromethanesulfonic acid was used. The results are given in Table 12.

Example 46

Example 43 was repeated except that 0.05 mmol of nickel naphthenate, 0.05 mmol of 1,2-bis(diphenylphosphino)ethane, 4 mmol of isoprene and 0.75 mmol of 1,1,1,3,3,3-hexafluoroisopropyl alcohol were used, and that 0.05 mmol of trifluoromethanesulfonic acid and 0.1 mmol of dimethyl sulfate were used in place of 0.1 mmol of trifluoromethanesulfonic acid. The results are given in Table 12.

TABLE 12

| | Selectivity of dimers (%) | TON | | |
|---|---|---|---|---|
| | | Total dimers | 4M1,2P | 4M1,2P + 2M1,2P |
| Example 43 | 74.4 | 30,100 | 13,900 | 26,800 |
| Example 44 | 81.1 | 19,700 | 9,250 | 17,000 |
| Example 45 | 50.6 | 22,800 | 4,290 | 18,200 |
| Example 46 | 79.1 | 25,600 | 11,200 | 22,400 |

(2M1,2P:2M1P + 2M2P)

Example 47-49

In a 50 ml Schlenk-type tube which had been cooled to 5° C. and filled with nitrogen, 4.7 ml of toluene containing 0.1 mmol of nickel naphthenate, 0.1 mmol of tricyclohexylphosphine (in 20% toluene solution) and 8 mmol of isoprene were charged, followed by the addition of 1 ml of toluene containing 1 mmol of triethylaluminum. The mixture was then heated to 18° C. with stirring.

The mixture was again cooled to 5° C. and water in an amount shown in Table 12 was gradually added thereto. Then 0.12 mmol of trifluoromethanesulfonic acid was added and 1.5 ml of toluene containing 1.5 mmol of 1,1,1,3,3,3-hexafluoroisopropyl alcohol was added in such manner that the internal temperature in the tube did not exceed 20° C.

In a stainless steel 500 ml autoclave which had been filled with nitrogen, the catalyst solution prepared as described above and 15 ml of toluene were introduced at 15° C. and the propylene was injected to a pressure of 4 Kg/cm²G to react at 10° C. for 1.5 hours.

After the reaction was completed, the reaction mixture was cooled to 5° C., followed by purging unreacted propylene from the mixture. Then it was analyzed by gas chromatography. The results are given in Table 13.

TABLE 13

| | Water/Ni (in mole) | Selectivity of Dimers (%) | TON Total dimers | TON DMB-1 + DMB-2 |
|---|---|---|---|---|
| Example 47 | 3 | 61 | 4,500 | 4,020 |
| Example 48 | 1.5 | 58 | 17,400 | 14,500 |
| Example 49 | 0.5 | 70 | 17,400 | 13,700 |

Example 50

Example 47 was repeated except that 1,2-bisdiphenylphosphinoethane was used in place of tricyclohexylphosphine and that trifluoromethanesulfonic acid was used in an amount of 0.2 mmol instead of 0.12 mmol. The results are given in Table 14.

TABLE 14

| | Selectivity of dimers (%) | TON Total dimers | 4M1,2P | 4M1,2P + 2M1,2P |
|---|---|---|---|---|
| Example 47 | 100 | 10,800 | 5,610 | 8,590 |

Example 51-53

In a 50 ml Schlenk-type tube which had been cooled to 5° C. and filled with nitrogen, 0.375 ml of toluene containing 0.01 mmol of nickel naphthenate, 0.01 mmol of tricyclohexylphosphine (in 20% toluene solution) and 0.8 mmol of isoprene were charged at 5° C., followed by the addition of 0.2 ml of toluene containing 0.2 mmol of triethylaluminum. The mixture then was heated to 18° C. with stirring.

The mixture was again cooled to 5° C. and 0.03 mmol of water was gradually added to it. Then methanesulfonic acid in an amount given in Table 14 was added and 0.7 ml of toluene containing 0.7 mmol of 2,4,6-trichlorophenol was added in such manner that the internal temperature in the tube did not exceed 20° C.

In a stainless steel 100 ml autoclave which had been filled with nitrogen, the catalyst solution prepared as described above and 2 ml of toluene were introduced at 15° C. and then propylene was injected to a pressure of 6 Kg/cm²G to react at a temperature between 15° C. and 20° C. for 1 hour.

After the reaction was completed, the reaction mixture was cooled to 5° C., followed by purging unreacted propylene from the mixture. Then it was analyzed by gas chromatography. The results are given in Table 15.

Comparative Example 4

Example 51 was repeated except that methanesulfonic was not used. The results are given in Table 15.

TABLE 15

| | Methanesulfonic acid/Ni (molar ratio) | Selectivity of dimers (%) | TON Total dimers | TON DMB-1 + DMB-2 |
|---|---|---|---|---|
| Example 51 | 3 | 72 | 46,633 | 30,358 |
| Example 52 | 5 | 65 | 42,768 | 27,264 |
| Example 53 | 7 | 66 | 45,641 | 29,072 |
| Comp. Exam. 4 | — | 55 | 6,020 | 5,069 |

The invention being thus described, it will be obvious that the same way be varied in many ways. Such variations are not to be regarded as a departure from the spirit and scope of the invention, and all such modifications as would be obvious to one skilled in the art are intended to be included within the scope of the following claims.

What is claimed is:

1. A process for preparing a dimer of a lower α-olefin comprising dimerizing an α-olefin in the presence of a catalyst system A which consists essentially of:
   (1) at least one nickel (II) compound selected from the group consisting of organic acid salts, inorganic acid salts and complex compounds of nickel,
   (2) a trialkylaluminum,
   (3) at least one compound selected from the group consisting of halogenated phenols of the general formula:

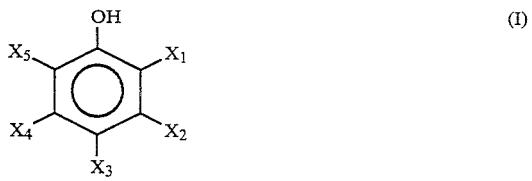

(I)

wherein $X_1$ to $X_5$ independently represent a halogen atom, a hydrogen atom, or a hydroxyl group, with the proviso that at least one of them is a halogen atom, and a fluorinated isopropyl alcohol, (4) at least one phosphorous compound selected from the group consisting of compounds of the formulae:

$PR^1R^2R^3$ (II)

$P(NR^4{}_2)_3$ (III)

$P(OR^5)_3$ (IV)

and

$PR^6R^7(CH_2)_nPR^6R^7$ (V)

wherein $R^1$, $R^2$, $R^3$, $R^4$, $R^5$, $R^6$ and $R^7$ independently represent an alkyl group, a cycloalkyl group, an aralkyl group or a phenyl group optionally substituted by alkyl groups or alkoxy groups and n is an integer from 1 to 6, and (5) at least one sulfur compound selected from the group consisting of sulfonic acids and dialkylsulfates; a catalyst system B which comprises:

(1) at least one nickel (II) compound selected from the group consisting of organic acid salts, inorganic acid salts and complex compounds of nickel, (2) a trialkylaluminum, (3) a fluorinated isopropyl alcohol, (4) at least one phosphorous compound selected from the group consisting of compounds of the formulae:

$PR^1R^2R^3$             (II)

$P(NR^4{}_2)_3$           (III)

$P(OR^5)_3$             (IV)

and $PR^6R^7(CH_2)_nPR^6R^7$     (V)

wherein $R^1$, $R^2$, $R^3$, $R^4$, $R^5$, $R^6$ and $R^7$ independently represent an alkyl group, a cycloalkyl group, an aralkyl group or a phenyl group optionally substituted by alkyl groups or alkoxy groups and n is an integer from 1 to 6, (5) a sulfonic acid and (6) water; or a catalyst system C which comprises:

(1) at least one nickel (II) compound selected from the group consisting of organic acid salts, inorganic acid salts and complex compounds of nickel, (2) a trialkylaluminum, (3) a halogenated phenol represented by the general formula:

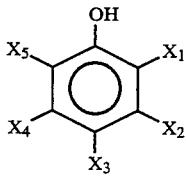

(I)

wherein $X_1$ to $X_5$ independently represent a halogen atom, a hydrogen atom, or a hydroxyl group, with the proviso that at least one of them is a halogen atom, (4) at least one phosphorous compound selected from the group consisting of compounds of the formulae:

$PR^1R^2R^3$             (II)

$P(NR^4{}_2)_3$           (III)

and $P(OR^5)_3$             (IV)

wherein $R^1$, $R^2$, $R^3$, $R^4$ and $R^5$ independently represent an alkyl group, a cycloalkyl group, an aralkyl group, or a phenyl group optionally substituted by alkyl groups or alkoxy groups, (5) a sulfonic acid and (6) water.

2. The process according to claim 1, wherein the catalyst system is Catalyst A.

3. The process according to claim 1, wherein the catalyst system is Catalyst B.

4. The process according to claim 1, wherein the catalyst system is Catalyst C.

5. The process according to claim 1, wherein the lower α-olefin is ethylene, propylene, or isobutene.

6. The process according to claim 2 wherein at least one compound selected from the group consisting of the halogenated phenols and the fluorinated isopropyl alcohols is a halogenated phenol.

7. The process according to claim 1, wherein in Catalyst A or B a molar ratio of the halogenated phenol to the trialkylaluminum is from 0.4 to 20.

8. The process according to claim 2, wherein the compound selected from the group consisting of the halogenated phenols and the fluorinated isopropyl alcohols is a fluorinated isopropyl alcohol.

9. The process according to claim 8, wherein the fluorinated iso-propyl alcohol is 1,1,1,3,3,3-hexafluoroisopropyl alcohol.

10. The process according to claim 3, wherein a molar ratio of the fluorinated isopropyl alcohol to the trialkylaluminum is from 0.2 to 10.

11. The process according to claim 1, wherein the trialkylaluminum is triethylaluminum.

12. The process according to claim 1, wherein a molar ratio of the trialkylaluminum to the nickel (II) compound is from 2 to 500.

13. The process according to claim 1, wherein a molar ratio of the phosphorous compound to the nickel (II) compound is from 0.1 to 50.

14. The process according to claim 1, wherein in Catalyst B or C a molar ratio of water to the nickel (II) compound is from 0.1 to 10 and a molar ratio of water to the trialkylaluminum is from 0.1 to 2.

15. The process according to claim 2, wherein the sulfur compound is a sulfonic acid and a dialkyl sulfate.

16. The process according to claim 2, wherein a molar ratio of the sulfur compound to the nickel (II) compound is from 0.1 to 20.

17. The process according to claim 1, wherein in Catalyst B or C a molar ratio of the sulfonic acid to the nickel (II) compound is from 0.1 to 20.

18. The process according to claim 1, wherein a concentration of the catalyst system is from $10^{-5}$ to $10^{-1}$ mol/liter in terms of a concentration of the nickel (II) compound.

19. The process according to claim 1, wherein a reaction temperature is from $-70°$ to $150°$ C.

20. The process according to claim 1, wherein a reaction pressure is from 0 to 30 Kg/cm²G.

* * * * *

UNITED STATES PATENT AND TRADEMARK OFFICE
CERTIFICATE OF CORRECTION

PATENT NO. : 5,349,115
DATED : September 20, 1994
INVENTOR(S) : Kotohiro Nomura, Masaru Ishino, Michio Yamamoto
Gohfu Suzukamo, Makoto Itagaki It is certified that error appears in the above-identified patent and that said Letters Patent is hereby corrected as shown below:

On the title page:

Under the heading [30] Foreign Application Priority Data, change "May 8, 1992 [JP]  Japan .......... 4-136730" to --May 28, 1992 [JP]  Japan ........ 4-136730--

Signed and Sealed this

Sixth Day of December, 1994

Attest:

BRUCE LEHMAN

*Attesting Officer*  *Commissioner of Patents and Trademarks*